United States Patent [19]

Steinman

[11] 4,122,034

[45] Oct. 24, 1978

[54] ANTIMICROBIAL COMPOSITIONS

[75] Inventor: Martin Steinman, Livingston, N.J.

[73] Assignee: Schering Corporation, Kenilworth, N.J.

[21] Appl. No.: 722,974

[22] Filed: Sep. 13, 1976

Related U.S. Application Data

[60] Division of Ser. No. 636,517, Dec. 1, 1975, Pat. No. 3,996,159, and a continuation-in-part of Ser. No. 314,899, Dec. 13, 1972, abandoned, said Ser. No. 636,517, is a division of Ser. No. 473,625, May 28, 1974, Pat. No. 3,944,672, which is a continuation-in-part of Ser. No. 314,899.

[30] Foreign Application Priority Data

May 22, 1975 [CA] Canada .................................. 227576

[51] Int. Cl.² ............................................. A61K 31/38

[52] U.S. Cl. .................................. 252/402; 252/401; 252/403; 252/406; 424/275

[58] Field of Search ............... 252/401, 405, 402, 403, 252/406; 424/274, 275, 285

[56] References Cited

PUBLICATIONS

Chemical Abstracts, 75:5699t (1971).
Chemical Abstracts, 76:140506p (1972).

*Primary Examiner*—Edward A. Miller
*Assistant Examiner*—Irwin Gluck
*Attorney, Agent, or Firm*—Bruce M. Eisen; Raymond A. McDonald

[57] ABSTRACT

Disclosed herein are 2-aminoalkyl-3-aryl-heteroindenes useful as antimicrobial agents.

1 Claim, No Drawings

ANTIMICROBIAL COMPOSITIONS

This is a division of application Ser. No. 636,517 filed Dec. 1, 1975, now U.S. Pat. No. 3,996,159, which in turn is a division of application Ser. No. 473,625 filed May 28, 1974, now U.S. Pat. No. 3,944,672 which in turn is a continuation-in-part of Ser. No. 314,899 filed Dec. 13, 1972, now abandoned.

This invention is also continuation-in-part of application Ser. No. 314,899 filed Dec. 13, 1972.

This invention relates to antimicrobial compounds and compositions containing them, to processes for their preparation, and to their use as antimicrobial agents. The compounds may be used in foods and in medicine and in industrial fields as antimicrobial agents. "Antimicrobial" as used herein refers to antibacterial, antifungal or antiprotozoal activity.

The antimicrobial compounds of the invention are 2-aminoalkyl-3-aryl-hetero-indenes of the formula:

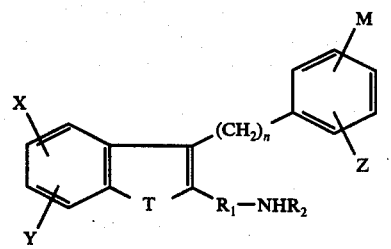

wherein $n$ is 0 or 1: $R_2$ is hydrogen or amino lower alkylene having 1 to 3 carbon atoms; $R_1$ is carbonyl or lower alkylene having 1 to 3 carbon atoms with the provisio that when $R_2$ is hydrogen, $R_1$ is lower alkylene; T is NH, S or O; X is halogen, nitro, or trifluoromethyl; Y is hydrogen, halogen, methyl or trifluoromethyl; M is hydrogen, halogen or methyl with the provisio that when X is nitro, M is halogen; Z is hydrogen, halogen, nitro or methyl; and the acid addition salts thereof.

"Heteroindene", as used herein, is an indene wherein the carbon atom in the 1-position is replaced by a hetero atom selected from $N_H$, S, or O, i.e. indole, benzothiophene and benzofuran, respectively.

As used herein the term "lower alkylene" refers to methylene, ethylene, propylene, and isopropylene and cyclopropylene. The term "halogen" as used herein comprehends fluorine, chlorine, bromine and iodine. Chloro is the preferred X substituent. A preferred location of the indole ring for the X moiety is the 5-position. Preferaby M is ortho-halo, with ortho-fluoro or ortho-chloro being especially preferred. T is preferably NH although it may be S or O. The term "amino lower alkylene" refers to radicals represented by the formula —$R_3$—$NH_2$ wherein $R_3$ is lower alkylene as defined above. "$n$" preferably is 0.

A particularly useful group of anti-microbial 2-aminoalkyl-3-phenyl-hetero-indenes within formula I has the formula:

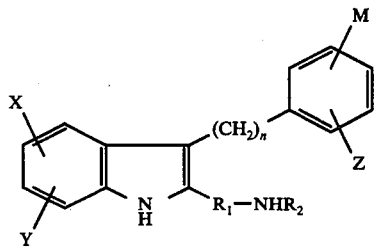

wherein $n$ is 0 or 1, X is halogen or trifluoromethyl, M is hydrogen, bromo or chloro, and one of Y and Z is 2-fluoro or 2-chloro and the other is hydrogen, halo, nitro or trifluoromethyl. It is particularly desireable for the M,Z-substituted phenyl group to be 2-fluorophenyl, 2,6-difluorophenyl, or 2,4-dichlorophenyl.

Particularly preferred compounds within this group include:
2-aminomethyl-5-chloro-3-(2-fluorophenyl)indole,
2-aminomethyl-5-chloro-3-(2,6-difluorophenyl)indole,
2-aminomethyl-5-chloro-3-(2,6-dichlorophenyl)indole,
2-aminomethyl-5-chloro-3-(2,4-dichlorophenyl)indole,
2-aminomethyl-5,7-dichloro-3-(2,4-dichlorophenyl)indole,
2-aminomethyl-5,6-dichloro-3-(2,4-dichlorophenyl)indole,
2-aminomethyl-6-chloro-3-(2,4-dichlorophenyl)indole,
2-aminomethyl-5-chloro-6-bromo-3-phenylindole, and
5,6-dichloro-3-(2,4-dichlorophenyl)indole-2-(N-β-aminoethyl)carboxamide.

Other particularly interesting compounds within formula I include:

2-(1-aminoethyl)-5-chloro-3-phenylindole,
2-(1-aminoethyl)-5-chloro-6-bromo-3-phenylindole,
2-aminomethyl-5-chloro-3-(benzyl)indole,
2-aminomethyl-5-chloro-3-(3,4-dichlorophenyl)indole, and
2-[N-(β-aminoethyl)aminoethyl]-5-chloro-3-phenylindole hydrochloride.

The acid addition salts can sometimes be used more conveniently than the indenes themselves; for example, because the salts have more convenient physical properties such as crystalline form or solubility, or because the salts are more readily purified by recrystallization, than the indenes. When the salts are used in food or medicine, the anion must, of course, be substantially non-toxic at the concentration or dosage used; when the salts are used in technical fields such as the preservation of paper, leather, or photographic goods, the anion need not necessarily be non-toxic.

Although some of the compounds of formula II have been proposed as intermediates in the preparation of benzodiazepines, many are novel; in particular, compounds in which M is halogen and/or Y and Z are not hydrogen are novel. Novel compounds within formula I include:

2-aminomethyl-5-chloro-3-(2,6-difluorophenyl)indole,
2-aminomethyl-5-chloro-6-bromo-3-phenylindole,
2-aminomethyl-5-chloro-3-(2,4-dichlorophenyl)indole,
2-(1-aminoethyl)-5-chloro-6-bromo-3-phenylindole, 2-aminomethyl-5,7-dichloro-3-(2,4-dichlorophenyl)indole,
2-aminomethyl-5,6-dichloro-3-(2,4-dichlorophenyl)indole,
2-aminomethyl-5-chloro-3-(3,4-dichlorophenyl)indole,
2-aminomethyl-5-chloro-3-(2,4-dichlorophenyl)-6-nitroindole,
2-aminomethyl-6-chloro-3-(2,4-dichlorophenyl)indole,
2-aminomethyl-5-iodo-3-(2,4-dichlorophenyl)indole,
2-aminomethyl-5-trifluoromethyl-3-(2,4-dichlorophenyl indole,
2-aminomethyl-6-chloro-3-(2,4-dichlorophenyl)indole,
2-aminomethyl-5-chloro-3-(3,4-dimethylphenyl)indole.

Still other compounds within the formula I are:

2-aminopropyl-7-iodo-3-(3-nitrophenyl)indole,
2-(2'-aminopropyl)-5-trifluoromethyl-3-(2-fluoro-4-nitrophenyl)indole,
2-aminomethyl-3-(2-nitrophenyl)indole,
2-aminopropyl-7-bromo-3-(2-trifluoromethylphenyl)indole.

The 2-aminoalkyl-3-phenylindenes of the formula II and their acid addition salts can be prepared by standard methods, know for the preparation of substituted indenes or of amines; for example, processes disclosed in the following literature: U.S. Pat. Nos. 3,697,508; 3,558,604 and 3,558,603; Belgian Pat. No. 724,993; and "Benzodiazepines", Inaba, Ishizumi and Yamamoto, *Chem. Pharm. Bull.*, 19(2), pages 263–272 (1971).

The 3-phenylindole nucleus itself is normally most conveniently obtained by a Fischer indole synthesis, or by an equivalent reaction in which a benzenediazonium salt reacts with an ester of a 2-benzylacetoacetic acid in the presence of alkali and the product is cyclised by heating in the presence of acid or in ethylene glycol. Further modifications, especially transformation of the substituent at the 2-position, and/or removal of a blocking or protecting group at the 1-position, may then be effected.

The 2-aminoalkyl-3-phenylbenzo [b] thiophenes can be prepared from methyl 3-phenylbenzo [b] thiophene-2-carboxylate, known from Krubsack and Higa in *Tetrahedron Letters* No. 47, page 4823 (1972), by standard methods. The 2-aminoalkyl-3-phenylbenzo [b] furans can be prepared from 2-cyano-5-chloro-3-phenylbenzofuran, known from standard methods.

Typical final steps are, reduction of a precursor compound of the formula:

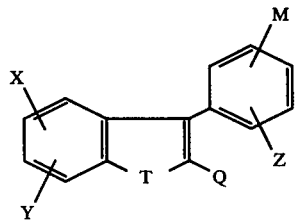

wherein Q is a group directly reducible to $R_1NHR_2$. The reduction can be effected by catalytic hydrogenation, by lithium aluminium hydride; electrolytically, etc.

A cyano group Q is most conveniently reduced with a boron hydride, especially borane, or with a complex metal hydride such as lithium aluminium hydride, calcium borohydride, or sodium borohydride in the presence of aluminium chloride or of boron trifluoride. The inert solvent will normally be an ether solvent, e.g., diethyl ether, tetrahydrofuran or dioxan. Compounds in which Q is a cyano group may also be reduced electrolytically.

Other suitable Q groups are carbamoyl or thiocarbamoyl, nitro alkyl, an oxime, ether or ester thereof, a ketimine, a hydrazine, or a semicarbazone.

Indenes wherein $R_2$ is an amino lower alkylene may be prepared by reaction of the corresponding carboxylate with the appropriate amine.

The 2-aminoalkyl-3-phenyl-heteroindenes may be isolated from the foregoing processes as the free bases or as acid addition salts or may be interconverted into acid addition salts e.g., hydrochlorate, sulfurate, nitrate, phosphate, acetate or succinate, phenolate and the like. The acid may be so chosen as to additionally impart activity, e.g. hexylresoicinol, to enhance the antimicrobial spectrum.

The following examples illustrate the preparation of compounds of the formula I; Example 1 shows the preparation of a preferred compound by the standard reduction of the corresponding nitrile with lithium aluminium hydride, whereas Example 2 illustrates a slightly different final step and also the preparation of the appropriate precursors. Examples 3 and 4 illustrates the most preferred compounds of the invention. Examples 5 and 6 respectively illustrate a thiophene and furan compound according to the invention, while Example 7 illustrates a preferred indole wherein $R_2$ is an amino lower alkylene.

EXAMPLE 1

2-Aminomethyl-5-chloro-3-(2-fluorophenyl)indole

Add a solution of 7.5 g. (0.0277 mol) of 5-chloro-3-(2-fluorophenyl)indole-2-carbonitrile in 100 ml of dry ether to a stirred suspension of 1.25 g. (0.033 mol) of lithium aluminium hydride in 200 ml of dry ether. Reflux the reaction mixture for 4 hours. Cool to room temperature and slowly add 3 ml of water to quench the reaction. Filter the mixture and dry overnight over magnesium sulfate.

Filter the solution, evaporate to dryness and recrystallize the residue from a mixture of methylene chloride and petroleum ether to give the title compound. The hexylresorcinol salt melts at 150°–152° C.

EXAMPLE 2

2-Aminomethyl-5-chloro-3-(2,6-difluorophenyl)indole

Step A:
N-[2-(2,6-difluorobenzoyl)-4-chloro]phenylglycinonitrile

A mixture of 5 g. (0.0186 mol) of 2-amino-5-chloro-2',6'-difluorobenzophenone, 3.9 g. (0.06 mol) of potassium cyanide and 2.8 g. (0.093 mol) of paraformaldehyde is treated with 25 ml of glacial acetic acid saturated with dry hydrogen chloride. The mixture is refluxed for 15 minutes, then poured onto 800 ml of ice water. The resulting precipitate is filtered off, washed with water and recrystallized from methanol (m.p. 175°–176°). Recrystallization affords yellow needles; m.p. 182°–183°.

Step B:
5-chloro-3-(2,6-difluorophenyl)indole-2-carbonitrile

A solution of N-[2-(2,6-difluorobenzoyl)-4-chloro]phenylglycinonitrile (2.0g) in 20 ml of dry tetrahydrofuran is treated with a large excess (4 ml) of trifluoroacetic anhydride. The mixture is refluxed for 4 hours, and solvent and excess of reagent are removed under vacuum. The residue is twice treated with dry tetrahydrofuran and each time evaporated to dryness. Finally, the residue is again dissolved in dry tetrahydrofuran and treated with 1 g of sodium hydride (57% in mineral oil).

The mixture is refluxed for one hour, cooled to room temperature and poured into a mixture of ice, water and chloroform. The organic layer is separated, washed with water and dried over magnesium sulfate. Filtration and evaporation yield a semisolid, which is filtered through silica gel to give the title compound; m.p. 199°–200°.

Step C: 2-aminomethyl-5-chloro-3-(2,6-difluorophenyl)indole

Borane in tetrahydrofuran (7 ml of a 1M solution) is added to a solution of 1 g (3.46 mmol) of 5-chloro-3-(2,6-difluorophenyl) indole-2-carbonitrile in 15 ml of dry tetrahydrofuran. The solution is stirred at room temperature for 2 hours and then refluxed for ½ and cooled to room temperature. 5 ml of 5N aqueous NCl is added dropwise and the mixture is refluxed for 20 minutes. The mixture is then poured onto a mixture of ice and aqueous 10 percent ammonia, and the precipitate is extracted with chloroform. The chloroform layer is washed with water and dried over magnesium sulfate, filtered and evaporated to dryness. Recrystallization from chloroform (charcoal) affords colorless crystals; m.p. 212°–214°.

EXAMPLE 3

2-Aminomethyl-6-bromo-5-chloro-3-phenylindole

Step A: Ethyl 6-bromo-5-chloro-3-phenylindole-2-carboxylate

Add 11 ml (33 g.) of bromine to a mixture of ethyl 5-chloro-3-phenylindole-2-carboxylate (30 g.) in 100 ml of acetic acid at 10°–20°. Stir overnight and then add a solution of sodium bisulfite. Filter and wash the precipitate with water. Stir the solid with methanol and filter to yield the title compound. Recrystallization from methanol yields the analytical sample; m.p. 205°–206° C.

Step B: 6-Bromo-5-chloro-3-phenylindole-2-carboxylic acid

Reflux the ester (13 g.) of step A in 100 ml of ethanol with 150 ml of 10% sodium hydroxide solution for 2 hours. Evaporate off most of the methanol and, after cooling the mixture, add 5% hydrochloric acid. Collect the precipitate and dry to obtain the title compound; m.p. 241°–242° C.

Step C: 6-Bromo-5-chloro-3-phenylindole-2-carboxamide

Mix the acid (6 g.) of step B with 20 ml of thionyl chloride and boil under reflux for 0.5 hour. Evaporate the solution to dryness. Add tetrahydrofuran and evaporate twice to remove any remaining thionyl chloride. Add tetrahydrofuran (80 ml) and bubble ammonia gas through the solution. Add water to dissolve the precipitate at which time an oil separates. Add methanol to the oil to yield crystals which are collected and dried to yield the title compound.

Step D: 6-Bromo-5-chloro-3-phenylindole-2-carbonitrile

Reflux the amide (4.5 g.) of step C with phosphorous oxychloride (20 ml) for 2 hours. Cautiously pour the mixture, while still hot, onto ice-water. Collect the precipitate and dry to yield the title compound.

Step E: 2-Aminomethyl-6-bromo-5-chloro-3-phenylindole

Reflux the nitrile (10 g.) of step D in 100 ml of 1 molar borane in tetrahydrofuran for 4 hours, cool and then cautiously add 7 ml of concentrated hydrochloric acid. Evaporate the solution and add 5% sodium hydroxide with stirring. Collect the solid, dissolve in ethanol and precipitate with water. Collect and dry the precipitate to yield the title compound. Recrystallize from benzene; m.p. 162°–163° C. The hydrochloride melts at 202°–204° C.

EXAMPLE 4

2-Aminomethyl-5-chloro-3-(2,4-dichlorophenyl)indole

Step A: N-[2-(2,4-dichlorobenzoyl)-4-chloro]phenylglycinonitrile

Mix together 2-amino-2',4',5-trichlorobenzophenone (5 g.), potassium cyanide (3.25 g.), and paraformaldehyde (2.5 g.). Then add 12.5 ml of acetic acid saturated with hydrogen chloride and 12.5 ml of acetic acid. Keep the temperature below 70° for several minutes and then boil under reflux for 5 minutes. Cool and pour onto ice-water. Collect the precipitate and extract with chloroform. Treat this solution with sodium carbonate solution and then water and finally dry (MgSO$_4$). Evaporate to yield the title compound. Recrystallize from methylene chloride-petroleum ether; m.p. 166°–167°.

Step B: 5-Chloro-3-(2,4-dichlorophenyl)indole-2-carbonitrile

Dissolve the glycinonitrile of step A (40 g.) in 175 ml of dry tetrahydrofuran. Add 50 ml of trifluoroacetic anhydride. Boil under reflux overnight. Remove the solvent under nitrogen. Add more solvent and remove twice. Dissolve the crystalline residue in tetrahydrofuran, and treat with 20 g. of 57% sodium hydride in mineral oil. Boil under reflux for 30 minutes and pour onto icewater. Stir and collect the solid. Wash with water, dry and wash with petroleium ether. Crystallize from methylene chloride-petroleum ether to obtain the title compound; m.p. 181°–182°.

Step C: 2-Aminomethyl-5-chloro-3-(2,4-dichlorophenyl)indole

Dissolve the nitrile (22 g.) of step B in a mixture of 137 ml of 1 molar borane in tetrahydrofuran and 100 ml of tetrahydrofuran and stir for 4 hours. Boil under reflux for 0.5 hour, cool and add 5 N hydrochloric acid. Boil under reflux for 1 hour and pour onto a mixture of ice and 10% ammonia. Extract with chloroform, wash and dry (MgSO$_4$). Evaporate to yield the title compound. Crystallize from ether-petroleum ether to obtain the analytical sample; m.p. 179°–180°. To prepare the hydrochloride salt, dissolve this material in ethanol, add concentrated hydrochloric acid, collect and dry the material; m.p. 226°–228°.

EXAMPLE 5

2-Aminoethyl-5-bromo-3-phenylbenzo[b]thiophene hydrochloride

Step A: Methyl 5-bromo-3-phenylbenzo[b]thiophene-2-carboxylate

Add 29.3 g. bromine (10 ml; 0.37 mole) to 8.0 g. (0.03 mole) of methyl 3-phenylbenzo[b]thiophene-2-carboxylate in 100 ml of acetic acid and stir the mixture overnight at room temperature. Add a saturated solution of sodium bisulfite. Decant the supernatant and wash the oil with water. Triturate with methanol. Recrystallize from methanol to yield the title compound; m.p. 125°–126°.

Step B: 5-Bromo-3-phenylbenzo[b]thiophene-2-carboxylic acid

Heat three grams of methyl 5-bromo-3-phenylbenzo[b]thiophene-2-carboxylate in a mixture of 50 ml of methanol and 30 ml of 10% sodium hydroxide, under reflux for 1 hour. Add concentrated hydrochloric acid to yield the title compound as a precipitate. Recrystallize from benzene; m.p. 265°–266°.

Step C: 5-Bromo-3-phenylbenzo[b]thiophene-2-carboxamide

Reflux 2.8 g. 5-bromo-3-phenylbenzo[b]thiophene-2-carboxylic acid (0.0084 mole) and 10 ml of thionyl chloride in 15 ml of dry tetrahydrofuran for one hour, evaporate to dryness, add 50 ml of tetrahydrofuran twice and evaporated each time to dryness. Dissolve acid in 70 ml of tetrahydrofuran, cool to about 10° and add with stirring 10 ml of concentrated ammonia. The title compound is obtained as a white solid; m.p. 201°–202°.

Step D: 5-Bromo-2-cyano-3-phenylbenzo[b]thiophene

Reflux 2.1 g. 5-bromo-3-phenylbenzo[b]thiophene-2-carboxamide (0.0063 mole) together with 10 ml. of phosphorus oxychloride for 1½ hours and then carefully pour onto ice water. Filter off the white precipitate. Dry. Recrystallize the title compound from methanol; m.p. 145°–146°.

Step E: 2-Aminomethyl-5-bromo-3-phenylbenzo[b]thiophene hydrochloride

Treat 1.4 g. 5-bromo-2-cyano-3-phenylbenzo[b]thiophene (0.0045 mole) in 40 ml of tetrahydrofuran, with 10 ml of 1 molar borane in tetrahydrofuran. Reflux the solution for 1½ hours. Slowly add 10 ml of 5% hydrochloric acid. Heat the mixture for ½ hour, cool and add sufficient sodium hydroxide solution to basicity. Extract the solution with ether and wash twice with water. Dry the ether layer (MgSO$_4$), filter and mix with 50 ml of ether saturated with hydrogen chloride. Dry the precipitate to yield the title compound; m.p. over 225° (decomp).

EXAMPLE 6

2-Aminomethyl-5-chloro-3-phenylbenzofuran hydrochloride

Treat 2.0 g. 2-cyano-5-chloro-3-phenylbenzofuran (0.008 mole) in 30 ml of tetrahydrofuran with 18 ml of borane in tetrahydrofuran (1 m solution). Reflux for 2 hours. Cool, add 10 ml of 10% hydrochloric acid and reflux for ½ hour. Evaporate the solution to dryness. Dissolve the residue in 50 ml of ethanol. Add 30 ml of ethanol saturated with hydrogen chloride. Dry the precipitate obtained to yield the title compound; m.p. 254°–256°.

EXAMPLE 7

5,6-dichloro-3-(2,4-dichlorophenyl)indole-2-N-(β-aminoethyl)carboxamide

Step A: Ethyl 5,6-dichloro-3-(2,4-dichlorophenyl)indole-2-carboxylate

Prepare a solution of 3,4-dichlorophenyl-diazonium chloride by treating 8.2 g. of 3,4-dichloroaniline in 25 ml of concentrated hydrochloric acid with a solution of 3.5 g. of sodium nitrite in 35 ml of water at −5°. Dissolve ethyl 2-(2,4-dichlorobenzyl) acetoacetate (14.3 g.) in 100 ml of ethanol with 8.3 g. of potassium hydroxide in 8.3 ml of water and cool to −5°. Add the solution of the diazonium salt to the latter solution, keeping the temperature at 0°, and stir for 15 minutes. Extract with ether and wash the ether solution with two 75 ml portions of 5% sodium hydroxide and then with water and dry (MgSO$_4$). Evaporate to yield the intermediate: ethyl 2,4-dichlorophenylpyruvate 3,4-dichlorophenyl hydrazone. The analytical sample is obtained from ethanol; m.p. 160°–161°. Dissolve the hydrazone (125 g.) in 700 ml of 20% ethanolic sulfuric acid and boil under reflux for 2 hours. Cool to room temperature and collect the crystalline product. Wash with 50% aqueous alcohol. Recrystallize from ethanol; m.p. 230°–231°.

Step B: 5,6-dichloro-3-(2,4-dichlorophenyl)indole-2-N-(β-aminoethyl)carboxamide Boil a mixture of 1.0 g. of ethyl 5,6-dichloro-3-(2,4-dichlorophenyl)indole-2-carboxylate, 1 ml of ethylene diamine and 5 ml of dry toluene under reflux for 24 hours. Then cool the mixture to room temperature, dilute with benzene, wash with water and dry over MgSO$_4$. Filter off the MgSO$_4$ and evaporate off the solvent to yield a solid residue, which upon crystallization from CHCl$_3$-petroleum ether gives the title compound; 600 mg; m.p. 216°–218°.

The following compounds may be prepared in a final step similar to that of Examples 1–7:

2-(1-aminoethyl)-6-bromo-5-chloro-3-phenylindole,
2-aminomethyl-5,7-dichloro-3-(2,4-dichlorophenyl)indole,
2-aminomethyl-5,6-dichloro-3-(2,4-dichlorophenyl)indole,
2-aminomethyl-5-chloro-3-(3,4-dichlorophenyl)indole,
2-aminomethyl-5-chloro-3-(2,4-dichlorophenyl)-6-nitroindole,
2-aminomethyl-6-chloro-3-(2,4-dichlorophenyl)-5-fluoroindole,
2-aminomethyl-3-(2,4-dichlorophenyl)-5-iodoindole,
2-aminomethyl-3-(2,4-dichlorophenyl)-5-trifluoromethylindole,
2-aminomethyl-6-chloro-3-(2,4-dichlorophenyl)indole,
2-aminomethyl-5-chloro-3-(2,4-dichlorophenyl)-6-methoxyindole,
2-aminomethyl-5-chloro-3-(2-fluorophenyl)benzo[b]thiophene,
2-aminomethyl-5,6-dichloro-3-(2-fluorobenzyl)benzo[b]thiophene,
2-aminomethyl-6-bromo-3-(2,6-dichlorobenzyl)benzofuran, 2-aminomethyl-3-(2-chloro-6-methyl-phenyl)indole,
2-aminomethyl-5-chloro-3-(3,4-dimethylphenyl)indole,
2-aminomethyl-5,6-dichloro-3-(2,4 dichlorophenyl)benzo[b]thiophene,
2-aminoethyl-5-iodo-3-(2,4 dichlorophenyl)benzo[b]thiophene,
2-aminomethyl-3-(2-chloro-6 methyl-benzyl)benzo[b]thiophene,
2-aminomethyl-5-chloro-3-(2,4 dimethylphenyl)benzofuran,
2-aminomethyl-5-chloro-3-(2-chloro-6-trifluoromethyl-benzyl)benzofuran,
2-aminomethyl-5-chloro-7-iodo-3-phenylbenzofuran hydrochloride,
5-chloro-3-(2-fluorophenyl)indole-2-N-($\beta$-aminoethyl)-carboxamide,
5,6-dichloro-3-(2,6-difluorophenyl)indole-2-N-($\beta$-aminoethyl)carboxamide,
5,6-dichloro-3-(2,4-dichlorobenzyl)indole-2-N-($\beta$-aminoethyl)carboxamide, and
2-[N-($\beta$-aminoethyl)aminoethyl]-5-nitro-3-(2,4-di-trifluoromethylphenyl)indole.

The compounds of formula I and their non-toxic acid addition salts can be used to treat diverse types of susceptible microbial infections. Furthermore, they are capable of preserving a wide variety of preparations including medical, veterinary, cosmetic and food preparations from microbial contamination: a stabilizing amount of such a compound is incorporated in the preparation in which the preservation is desired.

Susceptibility can be readily determined by standard in vivo and in vitro tests well known to the microbiologist. Genera of susceptible microorganisms include bacteria, fungi, and protozoa.

Exemplifying susceptible bacterial microorganisms are *Staphylococcus aureus, Streptococcus pyogenes C., Bacillus subtilis, Escherichia coli* and *Pseudomonas aeruginosa*. Susceptible fungi include *Candida albicans, Trichophyton mentagrophytes* and *Saccharomyces cerevisiae*. Susceptible protozoal pathogens include *Trychomonas vaginalis* and *Entamoeba histolytica*.

Tables I to VII give the results of various in vitro and in vivo tests of representative 2-aminoalkyl-3-phenylindenes of formula II against a variety of microorganisms including bacteria, fungi and protozoa, and also report the toxicity of these 2-aminoalkyl-3-phenylindenes. The compounds of the tests are as follows:

| Compound | Name |
|---|---|
| A | 2-aminomethyl-5-chloro-3-(2-fluoro-phenyl)indole |
| B | 2-aminomethyl-5-chloro-3-(2,6-difluoro-phenyl)indole |
| C | 2-(1-aminomethyl)-5-chloro-3-phenyl-indole |
| D | 2-aminomethyl-6-bromo-5-chloro-3-phenylindole |
| E | 2-aminomethyl-5-chloro-5-(2,4-dichlorophenyl)indole |

All the tests were carried out and (when necessary) scored under standard conditions. "MIC" means "minimum inhibitory concentration."

TABLE I

In vitro Antibacterial Activity of 2-aminoalkyl-3-phenyl-indoles of the formula I. Dilution in Mueller Hinton Agar pH 7.4

| | MIC (mcg/ml) Compound | | | | |
|---|---|---|---|---|---|
| Organism | A | B | C | D | E |
| Staphylococcus aureus | | | | | |
| 209P | 7.5 | 7.5 | 7.5 | 3.0 | 3.0 |
| Wood | 3.0 | 7.5 | 7.5 | 3.0 | 3.0 |
| Zeigler | 3.0 | 7.5 | 3.0 | 3.0 | 0.8 |
| Gray | 7.5 | 7.5 | 7.5 | 3.0 | 3.0 |
| 59N | 3.0 | 7.5 | 7.5 | 3.0 | 3.0 |
| Streptococcus pyogenes | | | | | |
| C | 7.5 | 17.5 | 7.5 | 3.0 | 3.0 |
| 27 | 7.5 | 7.5 | 7.5 | 3.0 | 3.0 |
| Cruz | 3.0 | 3.0 | 3.0 | 3.0 | 0.8 |
| Enterococcus 373 | 7.5 | 7.5 | 7.5 | 3.0 | 3.0 |
| 0928/72 | 7.5 | 17.5 | 7.5 | 3.0 | 3.0 |
| Escherichia coli | | | | | |
| 10536 | 7.5 | 7.5 | 7.5 | 3.0 | 3.0 |
| 1574-1 | 7.5 | 7.5 | 3.0 | 3.0 | 3.0 |
| 777 | 3.0 | 7.5 | 3.0 | 3.0 | 3.0 |
| 4195 | 3.0 | 7.5 | 3.0 | 3.0 | 3.0 |
| JR66 | 3.0 | 7.5 | 3.0 | 3.0 | 3.0 |
| Klebsiella AD17 | 7.5 | 17.5 | 7.5 | 3.0 | 7.5 |
| AD22 | 7.5 | 7.5 | 3.0 | 3.0 | 3.0 |
| G3694 | 7.5 | 7.5 | 3.0 | 3.0 | 3.0 |
| 3020 | 7.5 | 7.5 | 3.0 | 3.0 | 3.0 |
| 121 | 7.5 | 17.5 | 3.0 | 3.0 | 7.5 |
| Proteus mirabilis Hard | 17.5 | 17.5 | 7.5 | 3.0 | 3.0 |
| Peras | 7.5 | 37.5 | 7.5 | 3.0 | 17.5 |
| Proteus rettgeri mirabilis | 17.5 | 17.5 | 7.5 | 7.5 | 17.5 |
| Proteus vulgaris Napol | 17.5 | 17.5 | 7.5 | 3.0 | 3.0 |
| Proteus morganii Valz | 17.5 | 17.5 | 7.5 | 3.0 | 17.5 |
| Pseudomonas acruginosa | | | | | |
| 8709 | 17.5 | 17.5 | 17.5 | 7.5 | 7.5 |
| 762 | 17.5 | 17.5 | 37.5 | 17.5 | 17.5 |
| 130 | 17.5 | 17.5 | 17.5 | 17.5 | 7.5 |
| 138 | 17.5 | 17.5 | 17.5 | 7.5 | 17.5 |
| Trav. 1 | 17.5 | 17.5 | 17.5 | 7.5 | 17.5 |
| Salmonella ent. 1 | 7.5 | 7.5 | 7.5 | 3.0 | 3.0 |
| C$_2$Napc | 3.0 | 7.5 | 3.0 | 3.0 | 3.0 |
| B typhi | 7.5 | 7.5 | 3.0 | 3.0 | 3.0 |
| C$_1$ Oao | 7.5 | 7.5 | 3.0 | 3.0 | 3.0 |
| C$_2$ Cuban | 7.5 | 7.5 | 3.0 | 3.0 | 3.0 |

TABLE II

In vitro activity of 2-aminoalkyl-3-phenylindoles of the formula I against anaerobes in fluid Thioglycollate medium

| | MIC (mcg/ml) after 48 and 72 hrs. | | | | | | | | | |
|---|---|---|---|---|---|---|---|---|---|---|
| | Compound | | | | | | | | | |
| | A | | B | | C | | D | | E | |
| Organism | 48 | 72 | 48 | 72 | 48 | 72 | 48 | 72 | 48 | 72 |
| Bacteroides melaninogenicus | 7.5 | 7.5 | 7.5 | 17.5 | 7.5 | 7.5 | 3.0 | 3.0 | 3.0 | 3.0 |
| Bacteroides fragilis | 7.5 | 7.5 | 3.0 | 3.0 | 3.0 | 3.0 | .75 | .75 | .75 | .75 |
| Bacteroides corrodens | 7.5 | 7.5 | 7.5 | 7.5 | 3.0 | 3.0 | .75 | .75 | .75 | 3.0 |
| Eubacterium lentum | 17.5 | 17.5 | 17.5 | 17.5 | 7.5 | 7.5 | .75 | .75 | 3.0 | 3.0 |
| Clostridium novyi | 7.5 | 7.5 | 7.5 | 7.5 | 3.0 | 3.0 | .75 | .75 | .75 | .75 |
| Clostridium septicum | 7.5 | 7.5 | 3.0 | 3.0 | 3.0 | 3.0 | .75 | .75 | .75 | .75 |
| Clostridium histolyticum | 7.5 | 7.5 | 7.5 | 7.5 | 3.0 | 3.0 | .3 | .3 | .3 | .3 |
| Peptostreptococcus | 3.0 | 3.0 | 3.0 | 3.0 | 3.0 | 3.0 | .3 | .3 | .75 | .75 |

TABLE III

In vitro Anti-Candida Activity of 2-aminoalkyl-3-phenyl-indoles of the formula I. Dilutions in Sabouraud's Dextrose Agar MIC (mcg/ml) after 48 hours

| Candida albicans | A | B | C | D | E |
|---|---|---|---|---|---|
| Burke | 75 | 75 | 75 | 150 | 37.5 |
| Lusk | 75 | 75 | 75 | 75 | 37.5 |
| Blunden | 75 | 75 | 75 | 17.5 | 37.5 |
| Fix | 75 | 75 | 75 | 75 | 37.5 |
| Collins | 75 | 75 | 75 | 75 | 37.5 |
| Merkel | 75 | 75 | 75 | 75 | 37.5 |
| 29 | 75 | 75 | 37.5 | 75 | 37.5 |
| Wisconsin | 75 | 150 | 75 | 150 | 37.5 |
| Sparks | 75 | 150 | 75 | 150 | 37.5 |
| Bevan | 75 | 150 | 75 | 150 | 37.5 |
| Newcomb | 37.5 | 37.5 | 37.5 | 17.5 | 17.5 |
| Kennedy 1 | 37.5 | 75 | 37.5 | 17.5 | 37.5 |
| Pannell | 75 | 75 | 75 | 75 | 17.5 |
| Atkisson | 75 | 75 | 75 | 150 | 37.5 |
| 1 | 75 | 150 | 75 | 150 | 37.5 |
| 2 | 75 | 75 | 75 | 150 | 37.5 |
| 3 | 75 | 150 | 75 | 75 | 37.5 |
| 4 | 75 | 75 | 37.5 | 37.5 | 17.5 |
| 5 | 75 | 75 | 75 | 75 | 17.5 |
| 6 | 75 | 150 | 75 | 150 | 37.5 |
| 8 | 75 | 150 | 75 | 150 | 37.5 |
| 9 | 75 | 75 | 75 | 150 | 37.5 |
| Burnside | 75 | 150 | 75 | 75 | 37.5 |
| Lehtman | 75 | 150 | 75 | 150 | 37.5 |
| Fulcher | 75 | 75 | 75 | 75 | 37.5 |
| Shurelli | 75 | 150 | 75 | 150 | 37.5 |
| Frazier | 75 | 150 | 75 | 150 | 37.5 |
| Boyer | 75 | 150 | 75 | 150 | 37.5 |
| Sherod | 75 | 150 | 75 | 150 | 37.5 |
| Bognay | 75 | 75 | 75 | 75 | 37.5 |
| Johnson | 75 | 150 | 75 | 150 | 37.5 |
| Gay | 75 | 150 | 75 | 150 | 37.5 |
| Tyner | 75 | 150 | 75 | 75 | 37.5 |
| Kenndy 2 | 75 | 150 | 75 | 150 | 37.5 |
| Bertrand | 75 | 150 | 75 | 150 | 37.5 |
| Hons | 75 | 150 | 75 | 150 | 37.5 |

TABLE IV

In vitro Antifungal Activity of 2-amioalkyl-3-phenylindoles of the formula I against Dermetophytes and Aspergillus. Dilutions in Sabouraud's Dextrose Broth.

MIC (mcg/ml) after 96 hours

| Fungi | A | B | C | D | E |
|---|---|---|---|---|---|
| Trichophyton ascoides | 17.5 | 17.5 | 7.5 | 7.5 | 7.5 |
| discoides | 7.5 | 17.5 | 17.5 | 7.5 | 7.5 |
| ferrugineum | 7.5 | 37.5 | 17.5 | 17.5 | 7.5 |
| gallinae | 7.5 | 7.5 | 37.5 | 75.0 | 17.5 |
| megninii | 3.0 | 7.5 | 7.5 | 3.0 | 3.0 |
| mentagrophytes A | 7.5 | 7.5 | 7.5 | 7.5 | 3.0 |
| mentagrophytes B | 7.5 | 7.5 | 7.5 | 3.0 | 17.5 |
| mentagrophytes C | 7.5 | 7.5 | 3.0 | 3.0 | 17.5 |
| mentagrophytes Young | 7.5 | 7.5 | 7.5 | 7.5 | 3.0 |
| mentagrophytes H377 | 7.5 | 17.5 | 17.5 | 7.5 | 7.5 |
| rubrum Blehl | 7.5 | 17.5 | 37.5 | 7.5 | 3.0 |
| rubrum 3 | 7.5 | 17.5 | 17.5 | 3.0 | 3.0 |
| rubrum Haggerty | 7.5 | 17.5 | 7.5 | 7.5 | 3.0 |
| rubrum 360 | 7.5 | 17.5 | 7.5 | 3.0 | 3.0 |
| schoenleinii | 17.5 | 17.5 | 17.5 | 7.5 | 3.0 |
| schoenleinii 2 | 3.0 | 7.5 | 3.0 | 7.5 | 3.0 |
| soudenense | 17.5 | 17.5 | 17.5 | 3.0 | 7.5 |
| tonsurans | 17.5 | 200.0 | 7.5 | 17.5 | 7.5 |
| Tricoderm sp. | 7.5 | 7.5 | 7.5 | 7.5 | 3.0 |
| Microsporum nanum | 3.0 | 17.5 | 3.0 | 3.0 | 3.0 |
| Microsporum distortum | 3.0 | 17.5 | 7.5 | 3.0 | 3.0 |
| Epidermophyton floccosum | 3.0 | 17.5 | 17.5 | 7.5 | 3.0 |
| Aspergillus sp. No. 3 | 17.5 | 37.5 | 17.5 | 17.5 | 17.5 |
| Aspergillus niger 6275 | 17.5 | 37.5 | 17.5 | 17.5 | 17.5 |

TABLE V

Acute Toxicity of 2-aminoalkyl-3-phenylindoles of the formula I in mice.

| Compound | Acute LD$_{50}$ (mg/kg) | | |
|---|---|---|---|
| | I.P. | S.C. | Oral |
| A | 250 | 850 | >1000 |
| B | 225 | 900 | about 1000 |
| C | 100 | 600 | >1000 |
| D | 175 | 750 | about 950 |
| E | 85 | 540 | about 700 |

TABLE VI

Effect of some 2-aminoalkyl-3-phenylindoles of the formula II against topical T. mentagrophytes infections in guinea pigs.

| Compound | Concentration | Average No. of Days to become negative | | Average Sum of lesion scores | |
|---|---|---|---|---|---|
| | | Cultures | Lesion | Days 1–5 | Days 1–10 |
| A | 1% | 6.8 | 9.0 | 11.8 | 16.0 |
| " | 4% | 6.0 | 8.8 | 11.2 | 14.8 |
| B | 1% | 9.6 | 14.2 | 11.6 | 20.0 |
| " | 4% | 5.0 | 7.2 | 9.2 | 10.0 |
| C | 1% | 12.4 | 14.4 | 13.0 | 25.0 |
| " | 4% | 5.6 | 7.4 | 10.0 | 11.8 |
| D | 1% | >22 | >22 | 11.6 | 29.2 |
| " | 4% | 6.2 | 8.8 | 11.8 | 14.2 |
| E | 1% | >22 | >22 | 12.6 | 34.2 |
| " | 4% | 6.6 | 9.2 | 11.6 | 15.2 |
| Untreated controls | | >22 | >22 | 14.8 | 38.2 |

TABLE VII

In vitro Anti-Trichomonal Activity of some 2-aminoalkyl-3-phenyl-indenes of formula II.

| Compound | Minimal Level (mcg/ml) to Produce | |
|---|---|---|
| | 90% Suppression | 50% Suppression |
| A | 40 | 24 |
| B | 75 | 32 |
| C | 38 | 30 |
| D | 38 | 20 |
| E | 28 | 14 |

The invention, therefore, provides compositions containing, as an active ingredient, a 2-aminoalkyl-3-phenyl-heteroindene of the formula I hereinbefore defined or an acid addition salt thereof, in association with a suitable carrier, excipient or diluent. In its function as active ingredient, the compound of the formula I or salt thereof may be used to preserve the carrier from microbial contamination; for example, the carrier may be cutting or other oil, paper, leather, photographic emulsion, canvas or rope. If the salt is non-toxic, the carrier may also be a food-stuff, food-additive or food-supplement, or a medicinal or cosmetic preparation. Such medicinal or cosmetic preparations may conveniently be in fluid form, e.g., lotions, creams, ointments, solutions, suspensions or aerosol preparations.

When used as preservatives, the compounds of the formula I or their salts are preferably incorporated into the composition to be preserved in an amount of 0.05 to 1% by weight, especially 0.1 to 0.5% by weight.

The compounds of formula I and their non-toxic acid addition salts can themselves be used in medicine as anti-microbial agents, and thus may be formulated as pharmaceutical compositions containing at least one said compound or salt together with a pharmaceutical carrier or excipient. Such a composition may, for example, be in the form of shaped products, in particular dosage units, such as pills, tablets, capsules, dragees, lozenges or suppositories (especially vaginal suppositories). Alternatively, such compositions may be adapted for injection and therefore have as carrier a sterile, pyrogen-free injectable liquid. Injectable compositions will normally be in the form of dosage units; the various dosage units mentioned conveniently contain from 2 to 100 mg., preferably from 5 to 50 mg., of a compound of formula I or non-toxic acid addition salt thereof.

Compositions for oral administration, other than dosage units mentioned above, may be exemplified by powders, granulates, solutions, suspensions, elixirs, or aerosols. Compositions for topical application may be exemplified by ointments, creams, lotions, solutions, suspensions, aerosols, gels, shampoos, soaps or dusting powders. The compositions may be adapted in particular as ophthalmic, otic and nasal preparations. Such compositions will normally be based upon standard carriers such as those selected from pharmaceutically acceptable vegetable oils, pharmaceutically acceptable polyalkylene glycols, isopropanol, gelatin, benzyl alcohol, gums, glycerol, petrolatum, preservatives starch, sugars such as lactose, talc, magnesium stearate, aerosol propellants such as chlorofluoroalkanes, and coloring, flavoring, sweetening, thickening, suspending, dispersing, emulsifying, wetting, stabilising and buffering agents.

The composition may also be in the form of an animal feed-stock, feed-additive or feed-supplement.

Compositions in which the active ingredient is a compound of the formula I or non-toxic acid addition salt thereof preferably contain from 0.5 to 10% thereof.

A suitable parenteral dosage range of the compounds of the formula I and non-toxic acid addition salts thereof is about 2 to 10 mg./kg./day. The compounds of formula I and their non-toxic acid addition salts may be formulated into dosage forms as the sole active ingredient or used in association with other ingredients to extend the therapeutic spectrum.

The following formulations exemplify pharmaceutical compositions containing 2-aminoalkyl-heteroindenes of this invention; the active ingredient illustrated may, of course, be replaced with another compound of formula I or non-toxic acid addition salt thereof, e.g., compound D or E or especially B from the foregoing tests.

| Formulation 1 | |
|---|---|
| Topical Cream | Per kg. |
| 2-Aminomethyl-5-chloro-3-phenylindole | |
| Ethoxylated Cetyl/Stearyl Alcohol | 10 g. - 100 g. |
| | 20 g. |

| -continued | |
|---|---|
| Formulation 1 | |
| Topical Cream | Per kg. |
| Cetyl Alcohol | 35 g. |
| Stearyl Alcohol | 35 g. |
| Petrolatum | 200 g. |
| Mineral Oil | 50 g. |
| Buffers, Sufficient | — |
| Preservatives, Sufficient | — |
| Purified Water to make | 1.0 kg. |

Add the cetyl alcohol, stearyl alcohol, ethoxylated cetyl/stearyl alcohol, petrolatum and mineral oil to a suitable mixing vessel. Heat to 80° C. to melt. Mix. Add the preservatives, buffers and 2-aminomethyl-5-chloro-3-phenylindole in approximately 95% of the purified water heated to 80° C. in a suitable mixing vessel. Mix. Add the melted wax phase to the aqueous phase and mix while cooling to about 40° C. Add sufficient purified water to make 1 kg. Mix until cool.

| Formulation 2 | |
|---|---|
| Topical Ointment | Per kg. |
| 2-Aminomethyl-5-chloro-3-(2-fluorophenyl)indole | 10 g. - 100 g. |
| White Petrolatum, to make | 1.0 kg. |

Melt and heat the petrolatum to 50° C. in a suitable mixing vessel. Remove a portion of the melted petrolatum and make therewith a slurry of the 2-aminomethyl-5-chloro-3-(2-fluorophenyl)indole. Pass the slurry through a suitable colloid mill and mill until a uniform dispersion is obtained. Add the milled slurry to the remainder of the melted petrolatum and mix until cool.

| Formulation 3 | |
|---|---|
| Otic Suspension | mg/ml |
| 2-aminomethyl-5-chloro-3-(2-fluorophenyl)indole | 5 - 10 |
| Cetylpyridinium Chloride, NF | 0.20 |
| Glyceryl Triacetate | 880.0 |
| Polyethylene Glycol 200 q.s. ad | 1.0 ml |

Melt and heat the petrolatum to 50° C. in a suitable mixing vessel. Remove a portion of the melted petrolatum and make a slurry of the 2-aminomethyl-5-chloro-3-(2-fluorophenyl)indole. Pass the slurry through a suitable colloid mill and mill until a uniform dispersion is obtained. Add the milled slurry to the remainder of the melted petrolatum and mix until cool.

| Formulation 4 | | |
|---|---|---|
| Vaginal Tablets | mg/tablet | mg/tablet |
| 2-Aminomethyl-5-chloro-3-(2-fluorophenyl)indole | 10.0 | 5.0 |
| Lactose Hydrous, Impalpable powder USP | 772.0 | 777.0 |
| Sodium Lauryl Sulfate | 20.0 | 20.0 |
| Polyvinylpyrrolidone | 40.0 | 40.0 |
| Corn Starch, Food Grade | 150.0 | 150.0 |
| Magnesium Stearate | 8.0 | 8.0 |
| | 1000 mg | 1000 mg |

| Formulation 5 | |
|---|---|
| Intramuscular or Subcutaneous Oil Injection | mg/ml |
| 2-aminomethyl-5-chloro-3-(2-fluorophenyl)indole | 10 - 50 |

-continued

| Formulation 5 | |
|---|---|
| Intramuscular or Subcutaneous Oil Injection | mg/ml |
| Aluminium Monostearate, USP | 20.0 |
| Sesame Oil, Heated Treated, USP qs ad | 1.0 ml |

Formulations 6 to 8 illustrate compositions preserved with a 2-aminomethyl-3-phenylindole of the formula I:

| Formulation 6 | |
|---|---|
| Lotion | mg/ml |
| Betamethasone Valerate | 1.22 |
| 2-aminomethyl-5-chloro-3-(2-fluorophenyl) indole HCl | 1.00 |
| Mineral Oil, USP | 19.50 |
| Diethylene Glycol Monostearate S.E. | 6.50 |
| Cetostearyl Alcohol | 6.50 |
| Lanbritol Wax | 9.30 |
| Glycerin, USP | 50.00 |
| Isopropanol | 65.00 |
| Citric Acid | 0.08 |
| Purified Water, USP, to make | 1.00 ml |

| Formulation 7 | |
|---|---|
| Intramuscular or Intravenous Solution | mg/ml |
| Gentamicin (charged as sulfate) | 40.0 |
| Sodium Bisulfite, USP | 3.2 |
| Disodium Edetate, USP | 0.1 |
| 2-aminomethyl-5-chloro-3-(2-fluorophenyl)-indole (charged as the hydrochloride salt) | 1–3 |
| Water for Injection qs ad | 1.0 ml |

| Formulation 8 | |
|---|---|
| Aerosol Concentrate | mg/g |
| Megalomicin A Phosphate | 20.0 |
| 2-aminomethyl-5-chloro-3-(2-fluorophenyl) indole | 1.0 |
| Liquid Absorption Base | 90.0 |
| Stearic Acid | 25.0 |
| Glyceryl Monostearate | 25.0 |
| Isopropyl Myristate | 50.0 |
| Glycerol, USP | 100.0 |
| Alcohol SD 40 | 80.0 |
| Triethanolamine | 10.0 |
| Purified Water, USP, to make | 1.0 g |

This composition is packaged into a aerosol container with standard polyfluoroalkane propellant mixtures.

| Formulation 9 | |
|---|---|
| Topical Cream | Per kg. |
| 2-Aminomethyl-5-bromo-3- phenylbenzob]thiophene hydrochloride | 10 g. – 100 g. |
| Stearic acid | 60 g. |
| Propylene Glycol Monostearate | 100 g. |
| Isopropyl Myristate | 80 g. |
| Polyoxyethylene (20) Sorbitan Monopalmitate | 60 g. |
| Sorbitan Solution | 20 g. |
| Buffers, Sufficient | — |
| Preservatives, Sufficient | — |
| Purified Water to make | 1.0 kg. |

Add the stearic acid, propylene glycol monostearate, isopropyl myristate and polyoxyethylene (20) sorbitan monopalmitate to a suitable mixing vessel. Heat to 80° C. to melt. Mix.

It is further contemplated that the compounds of the present invention also have herbicidal, insecticidal and other biocidal activity. The compounds may have selective and/or broad base activity depending upon the specific compound within formula I and the specific use for which it is applied.

When used as a herbicide, the compounds may be applied to a stand of crops and weeds in the post-emergence treatment and to the ground in the pre-plant or pre-emergence treatment in a number of ways, well known to the art. The water-soluble compounds, such as the hydrochloride salts, may be sprayed simply as alcoholic/aqueous solutions. The compounds can be deposited as dusts containing a powdered carrier such as talc, attaclay, etc. The compounds having limited water solubility, such as the amine base itself, can be applied as emulsions, the same being formulated as is well known in the art, with commercially available surface-active agents. Among the surface-active agents utilizable are the sulfonated vegetable oils, sodium lauryl sulfate, Tween No. 20 (a polyalkylene ether alcohol), carbowax (polyethylene glycols of M.W. 1500 or more), Atlas G-2122 (polyoxyethylene glycol monolaurate), etc. Penetrants, sequestrants, mineral oils and cosolvents may also be included in the formulations. An example of a suitable formulation is given herein below:

Formulation 10

2-amino methyl-5-bromo-3-phenybenzo[b]thiophene hydrochloride ethanol.

This ethanol water formulation, when applied on the basis of 4–8 lbs. of amine base, may be used on a pre-emergence basis against weeds, such as barnyard grass, crabgrass and chickweed.

The compounds may be used as a dusting powder or spray as above described against insects such as ringworm and brown planthopper.

I claim:

1. A method for preserving a compound from microbial contamination, which comprises incorporating, in a composition in which preservation is desired, about 0.1 to 0.5% by weight of a compound of the formula:

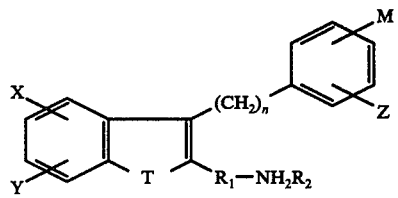

wherein $n$ is 0 or 1; $R_2$ is hydrogen, or lower amino alkylene having 1 to 3 carbon atoms; $R_1$ is carbonyl or lower alkylene having 1 to 3 carbon atoms with the provisio that when $R_2$ is hydrogen, $R_1$ is lower alkylene; T is S; M is hydrogen, halogen, methyl or trifluoromethyl; X is halogen, nitro, methoxy or trifluoromethyl; Y is hydrogen, halogen or methyl with the provisio that when X is nitro, Y is halogen; Z is hydrogen, halogen, nitro or methyl; and the non-toxic acid addition salts thereof.

* * * * *